(12) United States Patent
Tang et al.

(10) Patent No.: US 7,148,474 B2
(45) Date of Patent: Dec. 12, 2006

(54) DEVICE FOR TWO-DIMENSIONAL GAS-PHASE SEPARATION AND CHARACTERIZATION OF ION MIXTURES

(75) Inventors: Keqi Tang, Richland, WA (US); Alexandre A. Shvartsburg, Richland, WA (US); Richard D. Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 11/103,984

(22) Filed: Apr. 11, 2005

(65) Prior Publication Data

US 2006/0226353 A1    Oct. 12, 2006

(51) Int. Cl.
*H01J 49/40* (2006.01)
*H01J 49/26* (2006.01)
*B01D 59/44* (2006.01)

(52) U.S. Cl. ............... 250/287; 250/280; 250/281; 250/282

(58) Field of Classification Search ............... None
See application file for complete search history.

(56) References Cited

U.S. PATENT DOCUMENTS

| | | | | |
|---|---|---|---|---|
| 6,107,628 | A * | 8/2000 | Smith et al. | 250/292 |
| 6,323,482 | B1 * | 11/2001 | Clemmer et al. | 250/287 |
| 6,498,342 | B1 * | 12/2002 | Clemmer | 250/287 |
| 6,501,073 | B1 * | 12/2002 | Mylchreest et al. | 250/288 |
| 6,559,441 | B1 * | 5/2003 | Clemmer | 250/287 |
| 6,583,408 | B1 * | 6/2003 | Smith et al. | 250/288 |
| 6,674,071 | B1 * | 1/2004 | Franzen et al. | 250/292 |
| 6,690,004 | B1 * | 2/2004 | Miller et al. | 250/286 |
| 6,703,609 | B1 * | 3/2004 | Guevremont et al. | 250/287 |
| 6,707,037 | B1 * | 3/2004 | Whitehouse | 250/288 |
| 6,713,758 | B1 * | 3/2004 | Guevremont et al. | 250/290 |
| 6,730,904 | B1 * | 5/2004 | Wells | 250/292 |
| 6,818,890 | B1 * | 11/2004 | Smith et al. | 250/288 |
| 6,831,274 | B1 * | 12/2004 | Smith et al. | 250/288 |
| 6,906,319 | B1 * | 6/2005 | Hoyes | 250/282 |
| 6,943,347 | B1 * | 9/2005 | Willoughby et al. | 250/288 |
| 6,979,816 | B1 * | 12/2005 | Tang et al. | 250/288 |
| 6,987,262 | B1 * | 1/2006 | Guevremont | 250/288 |
| 7,005,632 | B1 * | 2/2006 | Miller et al. | 250/287 |
| 2002/0096631 | A1 * | 7/2002 | Andrien et al. | 250/288 |
| 2003/0038235 | A1 * | 2/2003 | Guevremont et al. | 250/287 |
| 2003/0070913 | A1 * | 4/2003 | Miller et al. | 204/192.1 |
| 2003/0089847 | A1 | 5/2003 | Guevremont et al. | |

(Continued)

OTHER PUBLICATIONS

"The Importance of Proper Grounding" <http://www.statefarm.com/consumner/vhouse/articles/grounding.htm>.*

(Continued)

*Primary Examiner*—Nikita Wells
*Assistant Examiner*—Bernard E. Souw
(74) *Attorney, Agent, or Firm*—Douglas E. McKinley, Jr.; Todd J. Harrington

(57) ABSTRACT

The present invention relates to a device for separation and characterization of gas-phase ions. The device incorporates an ion source, a field asymmetric waveform ion mobility spectrometry (FAIMS) analyzer, an ion mobility spectrometry (IMS) drift tube, and an ion detector. In one aspect of the invention, FAIMS operating voltages are electrically floated on top of the IMS drift voltage. In the other aspect, the FAIMS/IMS interface is implemented employing an electrodynamic ion funnel, including in particular an hourglass ion funnel. The present invention improves the efficiency (peak capacity) and sensitivity of gas-phase separations; the online FAIMS/IMS coupling creates a fundamentally novel two-dimensional gas-phase separation technology with high peak capacity, specificity, and exceptional throughput.

42 Claims, 5 Drawing Sheets

U.S. PATENT DOCUMENTS

| | | | |
|---|---|---|---|
| 2003/0168591 A1* | 9/2003 | Smith et al. | 250/288 |
| 2004/0004185 A9* | 1/2004 | Guevremont et al. | 250/287 |
| 2004/0232326 A1* | 11/2004 | Guevremont et al. | 250/287 |
| 2005/0006578 A1* | 1/2005 | Rockwood et al. | 250/289 |
| 2005/0040330 A1 | 2/2005 | Kaufman et al. | |
| 2005/0051719 A1 | 3/2005 | Miller et al. | |
| 2005/0092918 A1* | 5/2005 | Smith et al. | 250/288 |
| 2005/0151072 A1* | 7/2005 | Guevremont et al. | 250/282 |
| 2005/0269500 A1* | 12/2005 | Potvin et al. | 250/281 |

OTHER PUBLICATIONS

"Why do you have to use a separated conductor for grounding and for neutral?" General Information <http://www.epanorama.net/documents/groundloop/neutral_ground_separate.html>.*

"World Electric Guide" <http://kropla.com/electric.htm>.*

Purves et al., J. Am. Soc. Mass Spectrom. 2000, vol. 11, p. 738.

Purves et al., J. Am. Soc. Mass Spectrom. 2000, vol. 196, pp. 163-177.

Katta, V.; Chait, B.T., J. Am Chem. Soc. 1993, vol. 115, pp. 6317-6321.

Valentine, S.J. Clemmer, D.E., J. Am. Chem. Soc. 1997, vol. 119, pp. 3558-3566.

Clemmer, D.E., et al. Ion Mobility Measurements and their Applications to Clusters and Biomolecules, Jour of Mass Spec. vol. 32, 577-592 (1997).

R. Guevremont, High-field asymmetric waveform ion mobility spectrometry: A new tool for mass spectrometry, Elsevier, Jour. of Chromatography A, 1058 (2004) pp. 3-19.

Tang, et al., Three-Dimensional Gas Phase Separations for Analysis of Complex Ion Mixtures, Anal Chem (2004).

* cited by examiner

DEVICE FOR TWO-DIMENSIONAL GAS-PHASE SEPARATION AND CHARACTERIZATION OF ION MIXTURES

STATEMENT OF GOVERNMENT SUPPORT

This invention was made with United States Government support under Contract DE-AC05-76RL01830 awarded by the U.S. Department of Energy. The United States Government has certain rights in the invention.

BACKGROUND OF THE INVENTION

A significant challenge in both government and industry is the continued effort to increase the throughput of analytical applications (in particular, involving mass spectrometry), while controlling instrument costs and achieving the high resolution necessary to glean greater amounts of information about complex samples. Such information is useful in a wide variety of applications, ranging from life sciences (such as proteomics or modeling the biological functions of biomolecules in living organisms) to detection of chemical and biological agents of potential threat to national security.

Ion Mobility Spectrometry (IMS) and Field Asymmetric waveform Ion Mobility Spectrometry (FAIMS) are related gas phase techniques for rapid separation of complex mixtures and structural characterization of ions. Applications of both methods have greatly expanded since their coupling to electrospray ionization sources and mass-spectrometry. Coupling IMS to time of flight mass spectrometry (TOF MS) permitted simultaneous ion dispersion in the mobility and m/z dimensions. IMS is based on absolute ion mobility at low electric fields, while FAIMS exploits the mobility differences between high and low fields. Because of different physical mechanisms of IMS and FAIMS, the present invention couples FAIMS and IMS devices to achieve greater separation efficiency (resolving power). An extremely high ion separation speed of both FAIMS and IMS techniques makes this invention suitable for high throughput sample analyses. The general concept of the IMS system used in the present invention has been described and claimed in the U.S. Pat. No. 6,818,890, titled "High Performance Ion Mobility Spectrometry Using Hourglass Electrodynamic Funnel and Internal Ion Funnel" and is hereby explicitly incorporated into this disclosure by this reference.

SUMMARY OF THE INVENTION

The present invention relates to a device for separation and characterization of gas-phase ions. In one aspect of the present invention, a FAIMS analyzer is provided in communication with an IMS drift tube. The operating voltage applied to at least one of the FAIMS elements is preferably floated electrically on the voltage applied to at least one element of the IMS, supplied by a DC power supply. The present invention is generally applicable to any of the FAIMS instruments known to those having ordinary skill in the art. Accordingly, it is contemplated that the present invention may be successfully operated with FAIMS devices including, but not limited to, those having an axial longitudinal cylindrical geometry with or without a hemispherical terminus, a planar geometry, a cylindrical side-to-side geometry, or a spherical geometry.

In one embodiment of the present invention, an interface is interposed between the FAIMS and the IMS. Preferably, but not limiting, the interface is a capillary having an aperture of rectangular (slit), ellipsoidal, or circular geometry. The capillary may or may not be heated. In a further embodiment, the interface is an orifice having an aperture of rectangular (slit), ellipsoidal, or circular geometry. As with the capillary, the orifice may or may not be heated. The interface may also combine an orifice and a capillary configuration.

In another embodiment, an ion funnel is interposed between FAIMS and IMS instruments. The ion funnel may be of a regular or an hourglass design. Preferably, this configuration also includes an interface. In this embodiment of the present invention, it is also preferred that the FAIMS, the interface, and the ion funnel are electrically floated on a voltage applied to at least one element of the IMS drift tube. This embodiment also includes all of the various configurations of FAIMS and interface devices described above.

In each embodiment of the present invention, an ion detector may further be placed following IMS. An ion funnel may be interposed between the IMS and the detector. By way of example, and not meant to be limiting, the detector may comprise a mass spectrometer, such as a quadrupole mass spectrometer, a quadrupole ion trap mass spectrometer, a time-of-flight mass spectrometer, a Fourier transform ion cyclotron resonance mass spectrometer, a sector mass-spectrometer, or other detectors, including but not limited to a Faraday cage, an electron or a photo multiplier detector and a charge-coupled device (CCD detector).

Preferably, there is a control unit in communication with the power supply providing the voltage(s) to FAIMS, wherein a signal from the power supply indicating the voltage(s) supplied to FAIMS is communicated to the control unit. The control unit (for example, a computer) and the power supply may be at different potentials and electrically isolated from each other. Then the communication between the control unit and the power supply cannot be via a regular electrical cable, but has to be through other conductors including but not limited to an electrically isolated fiber optic cable, a wireless link, and an electrical cable featuring an isolation transformer. All such conductors as would be selected by a person of ordinary skill in the art are hereby incorporated, without limitation.

While the general characteristics of the present invention have been shown and described, the operations and advantages of the present invention are best illustrated by an example. Accordingly, experiments in which the present invention was reduced to practice and then operated to demonstrate the superior performance enabled by the present invention when compared to prior art methods were conducted and described below. However, the present invention should in no way be viewed as limited to either the specific device, or the operation of that device, as described below. Rather, these experiments are provided merely to illustrate one example of how the present invention may be reduced to practice and operated. Those skilled in the art will readily recognize that numerous departures from the specific details of the device and its operation shown below are possible, yet would still fall well within the more general description provide above, and set forth in the appended claims.

DESCRIPTION OF THE PREFERRED EMBODIMENTS

A device constructed to demonstrate the advantages and application of the present invention consists of seven sections: an ion source, a FAIMS analyzer, an interface between FAIMS and hourglass ion funnel, an hourglass ion funnel, an IMS spectrometer, an ion funnel, and an ion detector. Except as noted below, the device components are exhibited in the conceptual drawing shown in FIG. 1. While all voltages listed below are for positively charged ions (cations), those having ordinary skill in the art will immediately recognize that the polarities can readily be inverted to analyze negatively charge ions (anions). As will be recognized by one of ordinary skill in the art, a voltage is applied to the FAIMS to produce ion separations therein. A voltage is also applied to IMS to effect ion separations therein. In the device constructed to demonstrate the advantages and application of the present invention, all voltages applied to the FAIMS are floated on top of the voltage applied to the IMS drift tube.

Figure 1:
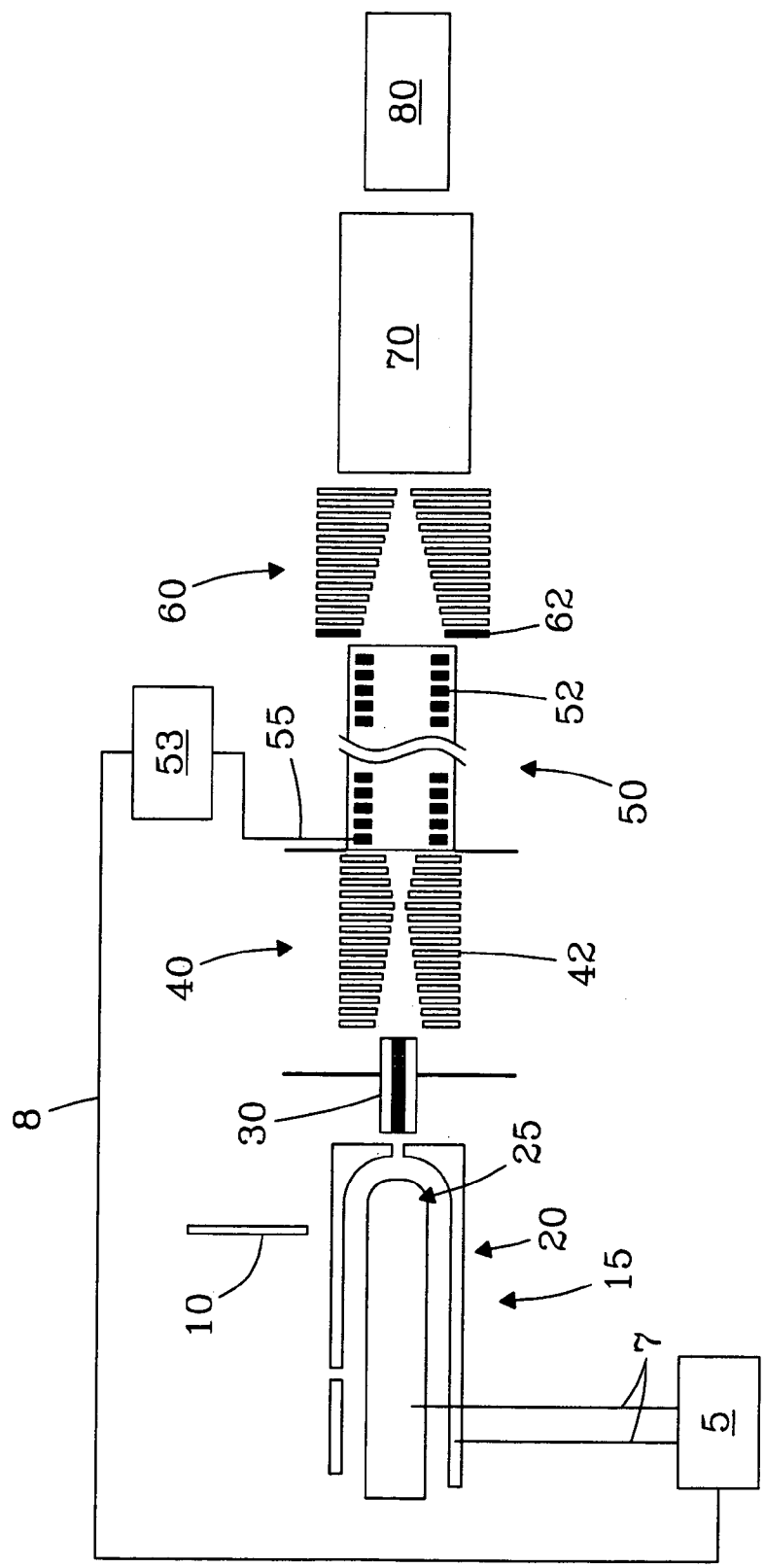
FIG. 1 is a schematic drawing of the present invention.

According to FIG. 1, a power supply 5 provides all voltages for FAIMS operation. The voltages are applied to the FAIMS via electrical conductors 7. The ion source section 10 comprises an electrospray ionization (ESI) source that generates solvated ions. The ions and other charged particles are introduced into a FAIMS operated typically (but not necessarily) at atmospheric pressure. The FAIMS power supply 5 is electrically floated on top of the IMS drift voltage by referencing the electrical ground of 5 to the output voltage of IMS power supply described herein using an electrical cable 8.

In operation of the device, an ESI emitter delivers the analyte solution pumped by a syringe pump through a capillary. Ions generated in ESI are sampled into sampling orifice of the FAIMS device. Ion desolvation is achieved by a counter flow of dried gas, typically nitrogen, that may be heated or at room temperature.

The FAIMS 15 is a commercial instrument available from Ionalytics (Ottawa, ON, Canada), here the Selectra model. FAIMS devices that may be successfully operated with the present invention include, but are not limited to, those having an axial longitudinal cylindrical geometry with or without a hemispherical terminus, a planar geometry, a cylindrical side-to-side geometry or a spherical geometry. The FAIMS uses a high-voltage, typically ±2500 V to ±4000V, asymmetric waveform to create an oscillating field between an outer electrode 20 and an inner electrode 25 perpendicular to the motion of the ions, which are propelled pneumatically between the electrodes. The FAIMS exploits the mobility differences between the high and low electric fields.

The ions exiting the FAIMS instrument 15 were sampled into an interface 30 between the FAIMS instrument 15 and an hourglass ion funnel 40. The interfaces 30 that may be successfully utilized in the present invention include, but are not limited to, an orifice or a capillary. The orifice or the capillary typically have 420 μm internal diameters. The interface 30 may or may not be heated, depending on the desired results.

Ions exiting the interface 30 are sampled into an hourglass ED funnel 40. Similarly to the ion funnel described in U.S. Pat. No. 6,818,890, the hourglass ED funnel 40 consists of a stack of ~100 metal plates 42 alternating with plastic plates for insulation and precise spacing, both plates ~0.5 mm thick for the total funnel length of ~10 cm. Each plate has a round hole in the center, with the i.d varying from 25 mm to 2 mm.

Each metal plate 42 features two pins on opposite sides, supplying the RF and DC potentials from the adjoining electrical connectors. The stack is held together and aligned by four parallel ceramic tubes with bolts inside. The bolts secure the funnel to a plastic (herein peek) disk of the IMS unit, as described below.

In the hourglass funnel disclosed herein, the i.d. decreases over a number of plates (here from 25 mm to 2 mm over 80 plates), then increases (here to ~12 mm over the next 20 plates). The last funnel plate carries only a DC potential (no RF). This plate may be covered with a mesh (here 1 mm. square mesh) to trap ions. In another embodiment, two last plates carry a DC voltage only. An hourglass funnel may feature (in the $1^{st}$ section of decreasing plate holes) a DC-only plate with a jet disrupter for ion intensity control, similar to that described in U.S. Pat. No. 6,583,408 "Ionization Source Utilizing a Jet Disturber in Combination with an Ion Funnel and Method of Operation".

Typical DC voltages on the ion source elements for the experiments described herein were (with respect to the IMS entrance potential): ESI needle (~2.0 kV), heated capillary (200 V), first funnel plate (190 V), jet disruptor (170 V), last funnel plate carrying an RF potential (40 V). The potential of last (DC-only) plate is periodically switched between the "closed" state (ions are trapped in the funnel) and "open" state (a packet of ions is released into IMS) by a rectangular DC pulse of desired length. Here, the voltages were 30 V and 100 V for open and closed states, respectively.

The drift tube 50 has a modular design, comprising an arbitrary number (in this instrument, up to ten) of nearly-identical units. Each unit is housed within a chamber, here a cylindrical steel tube ~20 cm. in diameter and 20 cm. long with wall thickness of ~2 mm. To join the units, each chamber features welded flanges on both ends, here standard 11-inch 8-bolt flanges with O-ring grooves. Some chambers are fit with insulated high-voltage feedthroughs and/or gas lines. Chambers are insulated and spaced apart by plastic (here ultra high molecular weight polyethylene or peek) disks ~1 cm. thick and ~30 cm. in diameter, and fastened by insulating bolts and nuts (here fiberglass-reinforced plastic). These disks have central holes to pass ions between units, and other holes and grooves for electrical connections, alignment, and securing the rods described below.

Each unit includes a stack of thin metal rings 52 (here 21 pieces) positioned and aligned on four parallel ceramic rods (here ~3 mm. in diameter), and insulated and spaced by plastic spacers. Here, rings 52 with the i.d. of ~55 mm and o.d. of ~80 mm are spaced ~10 mm apart. In one embodiment, one or more rings 52 immediately adjacent to the front ED funnel have a smaller i.d. close to the exit funnel diameter (here ~12 mm), which may improve the ion transmission into the IMS. The assembly is held between two plastic disks by insertion of rods into blind holes in the disks. Rings of any unit are consecutively connected by high-resistance resistors (here 1 MOhm), with same resistances between the units. The median (here 11$^{th}$) ring of each unit is electrically shorted to the chamber wall. The first and last rings of the whole tube are connected to outside voltages through vacuum feedthroughs.

At the entrance to the drift tube 50, the ED hourglass ion funnel 40 is mounted on the plastic disk of first unit as described above, so the last funnel plate is ~1 cm. away from the first IMS ring. At the exit to the drift tube 50, an internal ion funnel 60 is affixed to the plastic disk of last unit. The internal ion funnel 60 is identical to the ED funnel described above, except that it does not exhibit the hourglass shape, contains no jet disrupter, and its first electrode 62 has an aperture of 50 mm in diameter. Voltages applied to the elements of internal ion funnel also mirror those for the ED funnel.

The drift tube 50 contains buffer gas (here He or $N_2$) supplied through lines on the last section. In one embodiment, a cylindrical ring is inserted inside the chamber to let the gas in via a laminar, axially symmetric flow avoiding jet formation and turbulence. The pressure inside is monitored using a capacitance manometer (barotron). In the present design, the pressure inside can be varied from 1.5 to 22 Torr using a flow regulator. As will be apparent to those having skill in the art, higher pressures (up to 1 atm) would be attainable with smaller funnel apertures, extra stages of differential pumping, greater pumping capacity in the mass spectrometer (below), or some combination thereof.

The IMS drift voltage is generated by a high-voltage DC power supply 53 with a 50 kV range, monitored by a custom-made HV probe. This supply features a circuit that stabilizes the voltage output, and is current-limited for safety reasons. The drift voltage is loaded on the first ring of IMS drift tube by an electrical conductor 55. All voltages applied to FAIMS are floated on top of the drift voltage. Voltages routed to the ion source elements are provided by smaller power supplies also floated on top of the drift voltage. This includes the RF waveform on the ED funnel, supplied from normal power line via a high voltage isolation transformer. The drift voltage is partitioned linearly across the IMS length by the resistor chain described above. The chamber of each unit assumes the voltage of its median ring, thus minimizing the likelihood of electrical breakdown through the gas. To ensure the operator safety, exposed high voltages are contained within a grounded metal cage with controls and interlocks on the access doors.

A typical RF only quadrupole 70 may be utilized to assist the ion transmission from the IMS to the detector. The analysis of ion packets separated in IMS is performed by a commercial detector 80, typically a time-of-flight mass-spectrometer, for example a modified Q-Star® (MDS Sciex). This was used as supplied by the manufacturer, with certain modifications. The ion source, sampling interface, and skimmer of the Q-Star® were removed and replaced by a custom-built steel chamber that houses the ED funnel. This chamber is grounded. The OEM time-to-digital converter (TDC) was replaced by an Ortec™ TDC with a significantly improved performance. In another embodiment, an analog-to-digital (ADC) averager may be substituted for the TDC. This may be beneficial to extend the dynamic range in some regimes, for example at high signal intensities. The manufacturer's software designed for acquisition and processing of mass spectra has no time resolution, and thus was not used with the IMS data acquisition. To record individual ToF MS spectra along the IMS axis, replacement software was coded, providing the data archival and display in two dimensions.

Experiment:

The embodiment described above was then operated using a nano-electrospray ion source, a FAIMS separation stage of cylindrical geometry with a hemispherical terminus (Ionalytics Selectra™), a custom modular IMS drift tube of 210 cm length (ten sections) as described above, and modified Sciex Q-Star®. The entire FAIMS stage was electrically floated on the IMS drift voltage, up to 10 kV. Both the FAIMS/IMS and IMS/MS interfaces are implemented employing electrodynamic ion funnels. The FAIMS/IMS funnel employs an hourglass design with a 2-mm conductance limit aperture at the "neck" followed by a large trapping volume for efficient ion accumulation between IMS pulses and periodic injection of ion packets into the IMS. The IMS/MS funnel has an acceptance orifice matching the 2-in apertures of the IMS ring electrodes.

One skilled in the art readily recognizes that the useful separation power (e.g. total peak capacity) obtainable in a multi-dimensional separation depends on the orthogonality between the separation stages. The mutual orthogonality of all 3 stages of FAIMS/IMS/MS combination was evaluated using a sample mixture of 11 proteins (bovine serum albumin, bovine carbonic anhydrase, bovine beta-lactoglobulin, bovine serotransferrin, rabbit glyceraldehyde-3-phosphate dehydrogenase, *E. coli* beta-galactosidase, bovine alpha-lactalbumin, equine skeletal muschle myoglobin, chickin ovalbumin, bovine cytochrome c, rabbit phosphorylase b) digested with trypsin and 19 peptides (angiotensin, bradykinin fragment 2–9, bradykinin, try bradykinin acetate salt, des pro ala bradykinin, tyr c peptide, dynorphin A porcine fragment 1–13, epidermal growth factor receptor fragment 661–681, fibrinopeptide A, 3×FLAG®Peptide, diazepam binding inhibitor, leptin fragment 93–105 human, neurotensin, osteocalcin fragment 7–19 human, presenilin-1 N-terminal peptide, ProteoMassäP14R MALDI-MS standard, [Ala92]-peptide 6, syntide 2, vasoactive intestinal peptide fragment 1–12 human, porcine, rat). All chemicals were purchased from Sigma (St. Louis, Mo.) and used without further purification. Protein samples were digested by trypsin and mixed with the peptide mixture in 50:50 methanol:water+1% acetic acid. The mixture was infused to the ESI source at 0.4 μl/min.

Figure 2:
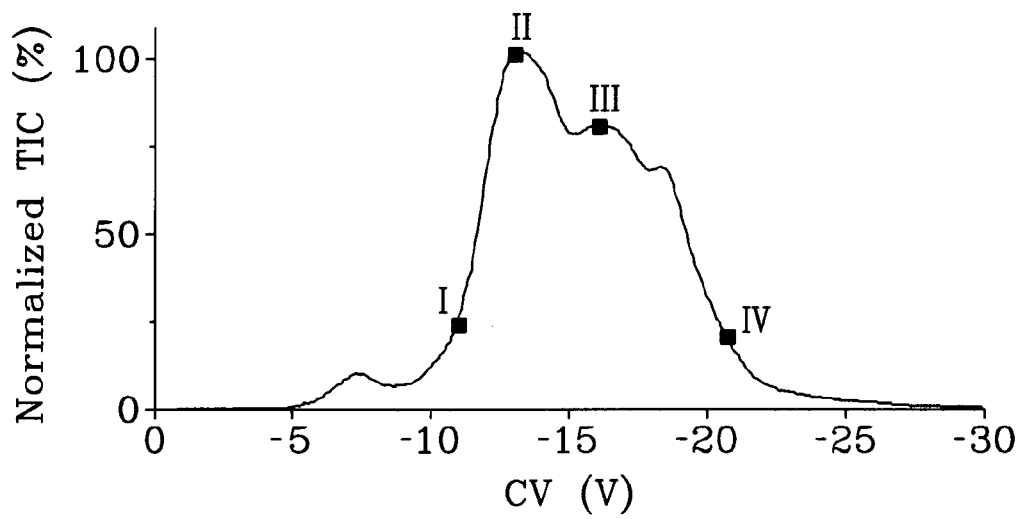
FIG. 2 shows FAIMS compensation voltage (CV) spectrum
Figure 3:
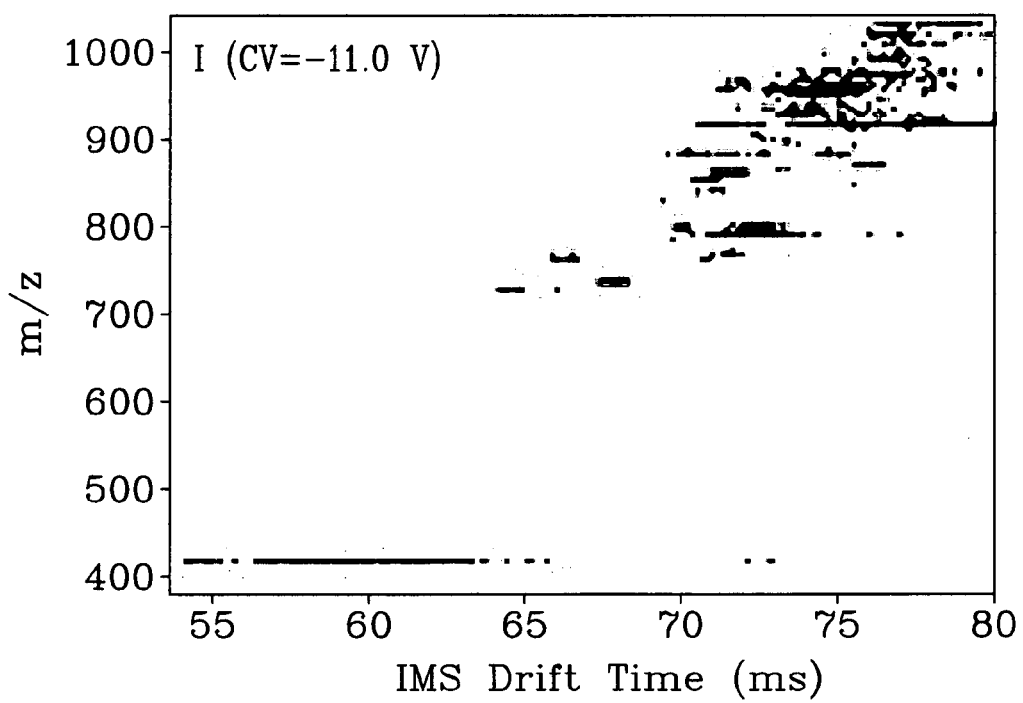
FIG. 3 shows two-dimensional peptide IMS (drift time vs. m/z) plots for compensation voltage of −11.0 V
Figure 4:
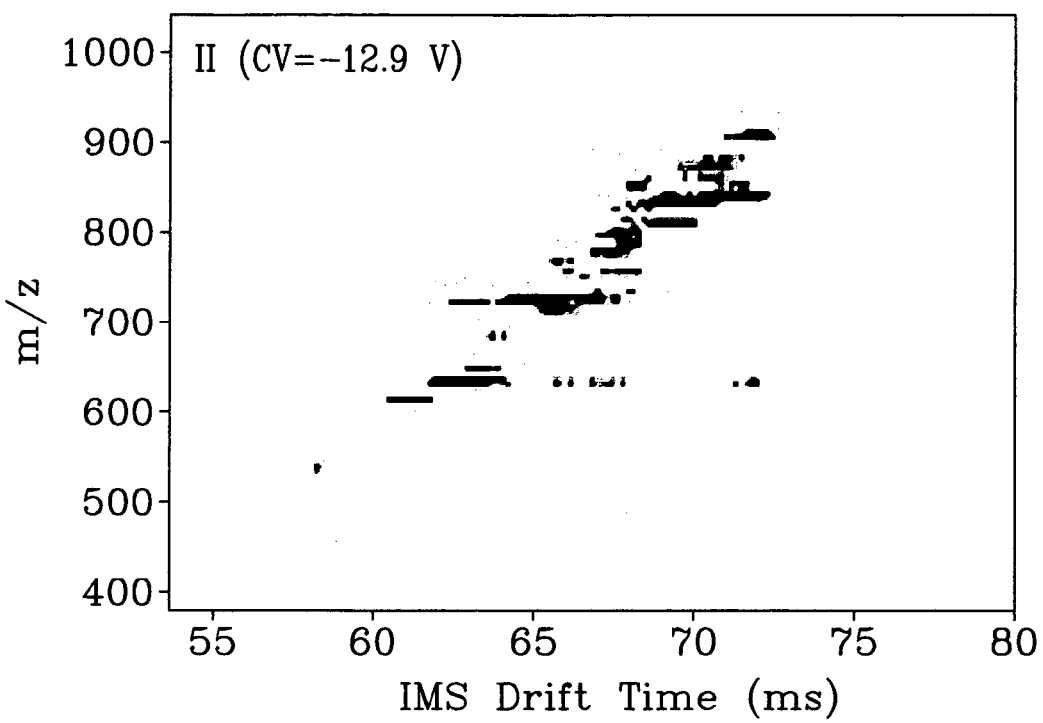
FIG. 4 shows two-dimensional peptide IMS/MS (drift time vs. m/z) plots for compensation voltage of −12.9 V
Figure 5:
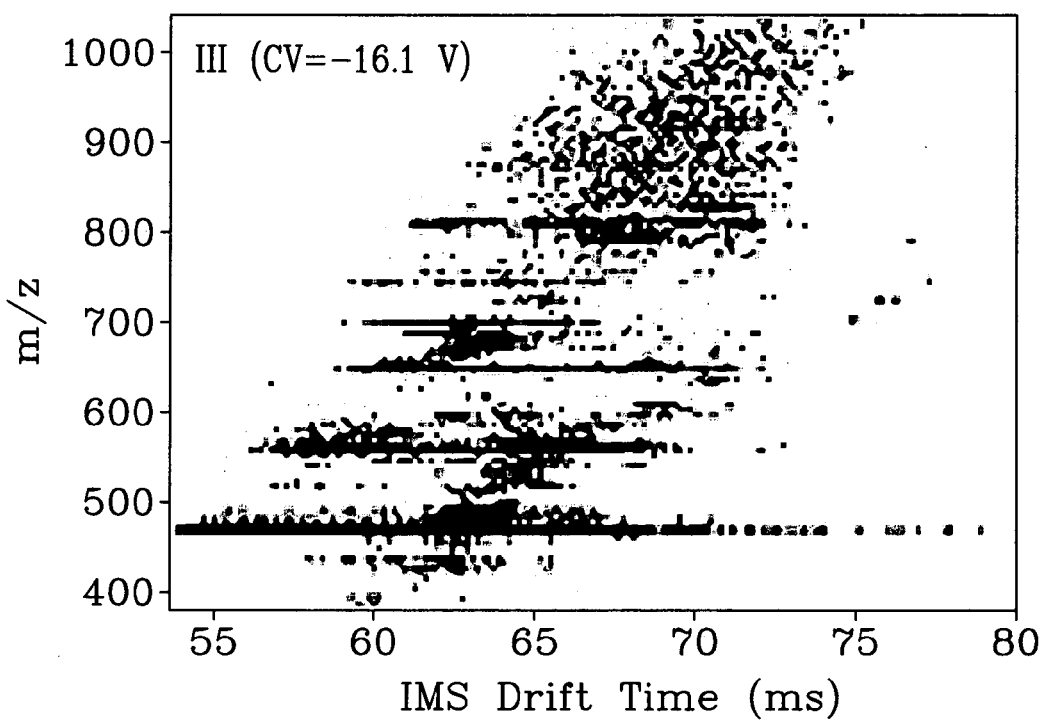
FIG. 5 shows two-dimensional peptide IMS/MS (drift time vs. m/z) plots for compensation voltage of −16.1 V
Figure 6:
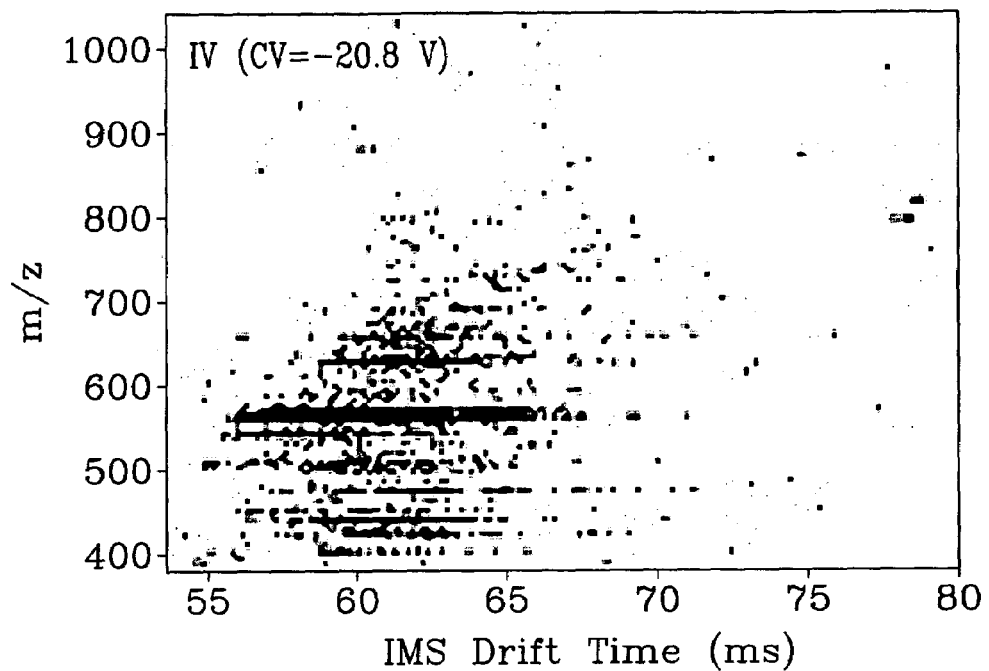
FIG. 6 shows two-dimensional peptide IMS/MS (drift time vs. m/z) plots for compensation voltage of −20.8 V

The FAIMS compensation voltage (CV) spectrum shown in FIG. 2 was acquired using a −4 kV dispersion voltage (DV) and a 50:50 $N_2$:He mixture. The 210 cm long IMS drift tube was operated at 4 kV drift voltage and 4 Torr of $N_2$ buffer gas.

FIG. 3–FIG. 6 show the two-dimensional IMS (drift time)/MS (m/z) plots acquired across the range of CVs. Significant correlation exists between IMS and MS separations as evidenced in the subset of peptides in FIG. 3 and FIG. 4 (CV=−11 V and −12.9 V for 2+ ions) and FIG. 5 and FIG. 6 (CV=−16 V for 2+ and 3+ ions; CV=−20.8 V for mostly 3+ ions). The orthogonality of the FAIMS separation to both IMS and MS is demonstrated by the different patterns in FIG. 3–FIG. 6.

Figure 7:
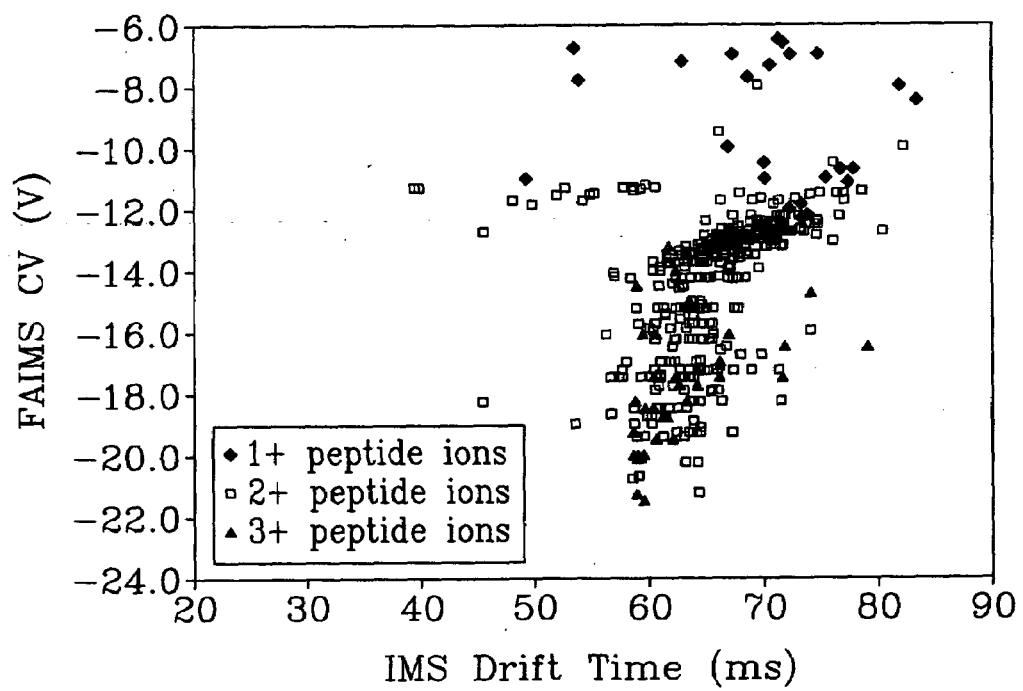
FIG. 7 shows compensation voltages and drift times for 189 peptides

FIG. 7 shows the peak CVs and drift times for 189 peptides from the mixture. The significant orthogonality between FAIMS and IMS indicates that combined FAIMS-IMS-MS provides higher separation efficiencies than either IMS-MS or FAIMS-MS alone.

Figure 8:
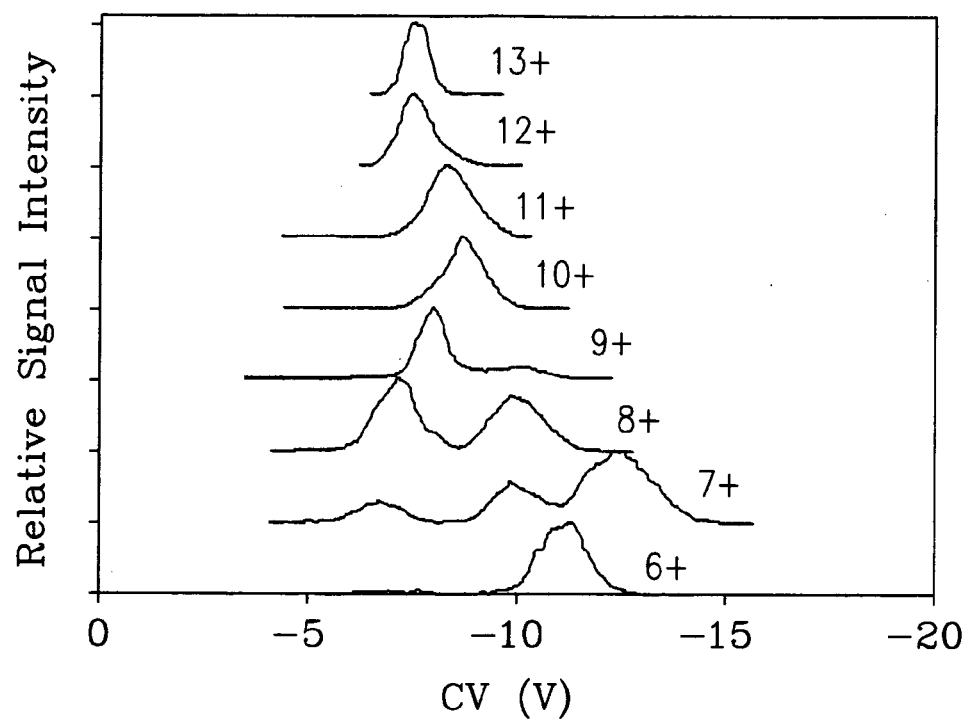
FIG. 8 shows relative ion signal vs. compensation voltage behavior for the 6+ and 13+ protonation states of ubiquitin

FIG. 8 shows the relative ion signal versus CV behavior for the 6+ to 13+ protonation states produced by ESI of denatured bovine unbiquitin at 0.4 μl/min flow rate and using a 50:50 methanol/water ratio plus 1% acetic acid. The multiple peaks for the lower charge states correspond to different gas phase conformations of ions.

Figure 9:
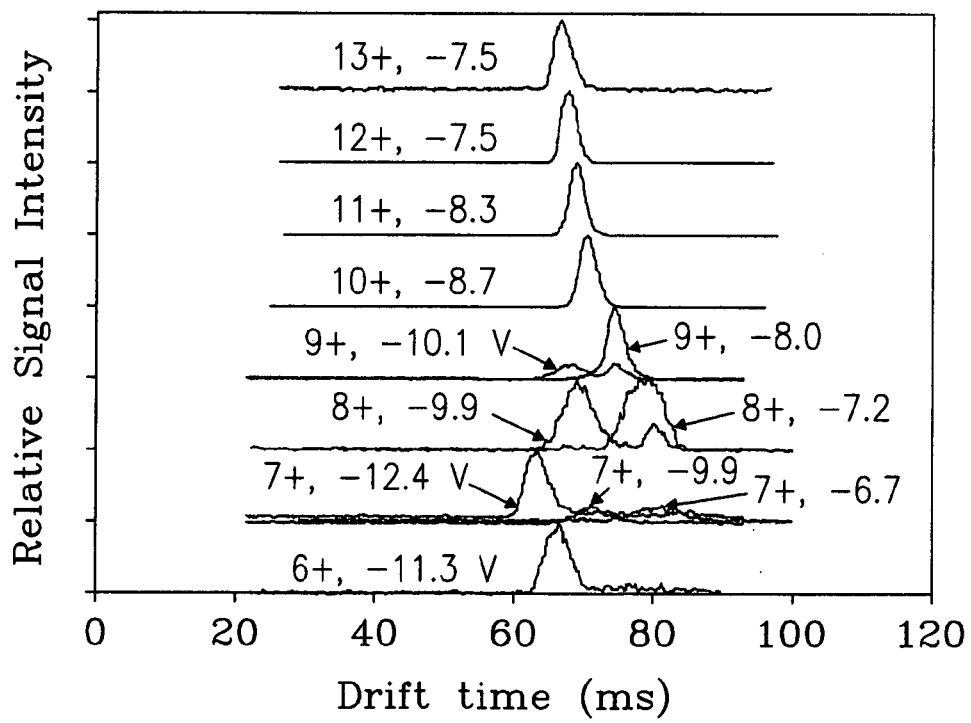
FIG. 9 shows mobilities of each significant FAIMS peak and each ubiquitin charge state

FIG. 9 shows the different mobilities of each significant FAIMS peak and each ubiquitin charge state. The FAIMS and IMS results are consistent with previous reports of structural variations depending on the charge state (Purves et al., *J. Am. Soc. Mass Spectrom.* 2000, Vol. 11, pg. 738; Purves et al., *Int. J. Mass Spectrom.* 2000, Vol. 196, pgs 163–177; Katta, V.; Chait, B. T. *J. Am. Chem. Soc.* 1993, Vol. 115, pgs. 6317–6321; Valentine, S. J.; Clemmer, D. E. *J. Am. Chem. Soc.* 1997, Vol. 119, pgs 3558–3566.) Additionally, the existence of multiple IMS peaks are revealed for the 7+ to 9+ charge states for a given CV, which implies that either additional ion conformations exist for these charge states that are not resolved by FAIMS or, more likely, some ions undergo a charge state change (e.g. by deprotonation) or a structural transition takes place between the FAIMS and IMS separation stages. The fact that the smaller peaks are at a higher CV and longer drift time peaks for the 9+ and 8+ species (approximately 82 ms at CV=−9.9 V) indicates that these ions have a somewhat extended structure on average compared to the 8+ ions obtained at lower CV (−7.2 V), consistent with their origin from 9+ ions having somewhat different structure.

In a further embodiment, the FAIMS stage was powered by a Selectra™ power supply that is commercially available from Ionalytics (Ottawa, ON, Canada). The FAIMS software was installed on a Dell Precision 200, operated with Window NT software, to control and operate the FAIMS instrument.

While a preferred embodiment of the present invention as been shown and described, it will be apparent to those skilled in the art that many changes and modifications may be made without departing from the spirit of the invention in its broader aspects. The appended claims are therefore intended to cover all such changes and modifications as fall within the true spirit and scope of the invention.

We claim:

1. A device for separation and characterization of gas-phase ions comprising a field asymmetric waveform ion mobility spectrometer in communication with an ion mobility spectrometer wherein the voltage applied to at least one element of the field asymmetric waveform ion mobility spectrometer is floated electrically on the voltage applied to at least one element of the ion mobility spectrometer.

2. The device of claim 1, wherein said field asymmetric waveform ion mobility spectrometer is configured in an axial longitudinal cylindrical geometry.

3. The device of claim 2, wherein said ion mobility spectrometer has a hemispherical terminus.

4. The device of claim 1, wherein said field asymmetric waveform ion mobility spectrometer is configured in a planar geometry.

5. The device of claim 1, wherein said field asymmetric waveform ion mobility spectrometer is configured in a cylindrical side-to-side geometry.

6. The device of claim 1, wherein said field asymmetric waveform ion mobility spectrometer is configured in a spherical geometry.

7. The device of claim 1, further comprising an interface interposed between said field asymmetric waveform ion mobility spectrometer and said ion mobility spectrometer.

8. The device of claim 7, wherein said interface is selected from the group consisting of a capillary, an orifice and any combination thereof.

9. The device of claim 7, wherein at least part of said interface is heated.

10. The device of claim 7, wherein the aperture of said interface has a geometry selected from the group consisting of a rectangular (slit), ellipsoidal, circular, and any combination thereof.

11. The device of claim 7, wherein the voltage applied to at least one element of said interface is floated electrically on the voltage applied to at least one element of the ion mobility spectrometer.

12. The device of claim 1, further comprising an ion funnel interposed between said field asymmetric waveform ion mobility spectrometer and said ion mobility spectrometer.

13. The device of claim 12, wherein the voltage applied to at least one element of said ion funnel is floated electrically on the voltage applied to at least one element of the ion mobility spectrometer.

14. The device of claim 12, wherein said ion funnel has an hourglass design.

15. The device of claim 7, further comprising an ion funnel interposed between said interface and said ion mobility spectrometer.

16. The device of claim 15, wherein said ion funnel has an hourglass design.

17. The device of claim 15, wherein the voltage applied to at least one element of said ion funnel is floated electrically on the voltage applied to at least one element of the ion mobility spectrometer.

18. The device of claim 1, further comprising a detector in communication with said ion mobility spectrometer.

19. The device of claim 18, further comprising an ion funnel interposed between said ion mobility spectrometer and said detector.

20. The device of claim 18, wherein said detector is a mass spectrometer.

21. The device of claim 20, wherein said mass spectrometer is selected from the group consisting of a quadrupole mass spectrometer, a quadrupole ion trap mass spectrometer, a time-of-flight mass spectrometer, a Fourier transform ion cyclotron resonance mass spectrometer, and a sector mass spectrometer.

22. The device of claim 18, wherein said detector is selected from the group consisting of a Faraday cage, an electron or a photo multiplier detector, and a charge-coupled device.

23. The device of claim 1 further comprising a control unit in communication with a power supply wherein said power supply provides said voltage to at least one element of the field asymmetric waveform ion mobility spectrometer and wherein said control unit and said power supply are at different potentials and electrically isolated from each other.

24. The device of claim 23, wherein said control unit is at ground potential.

25. The device of claim 23 wherein said communication is implemented via means selected from the group consisting of a fiber optic cable, a wireless link, an electrical cable featuring an isolation transformer, and a combination thereof.

26. The device of claim 23, wherein said control unit is a computer or a computer board.

27. The device for separation and characterization of gas-phase ions comprising a field asymmetric waveform ion mobility spectrometer in communication with an ion funnel, and said ion funnel in communication with an ion mobility spectrometer.

28. The device of claim 27, wherein said ion funnel has an hourglass design.

29. The device of claim 27, wherein said field asymmetric waveform ion mobility spectrometer is configured in an axial longitudinal cylindrical geometry.

30. The device of claim 29, wherein said ion mobility spectrometer has a hemispherical terminus.

31. The device of claim 27, wherein said field asymmetric waveform ion mobility spectrometer is configured in a planar geometry.

32. The device of claim 27, wherein said field asymmetric waveform ion mobility spectrometer is configured in a cylindrical side-to-side geometry.

33. The device of claim 27, wherein said field asymmetric waveform ion mobility spectrometer is configured in a spherical geometry.

34. The device of claim 27, further comprising an interface interposed between said field asymmetric waveform ion mobility spectrometer and said ion funnel.

35. The device of claim 34, wherein said interface is selected from a group consisting of a capillary, an orifice, and any combination thereof.

36. The device of claim 34, wherein at least a part of said interface is heated.

37. The device of claim 34, wherein the aperture of said interface has a geometry selected from the group consisting of a rectangular (slit), ellipsoidal, circular, and any combination thereof.

38. A device of claim 27, further comprising a detector in communication with said ion mobility spectrometer.

39. The device of claim 38, further comprising an ion funnel interposed between said ion mobility spectrometer and said detector.

40. The device of claim 38, wherein said detector is a mass spectrometer.

41. The device of claim 40, wherein said mass spectrometer is selected from the group consisting of a quadrupole mass spectrometer, a quadrupole ion trap mass spectrometer, a time-of-flight mass spectrometer, a Fourier transform ion cyclotron resonance mass spectrometer, and a sector mass spectrometer.

42. The device of claim 38, wherein said detector is selected from the group consisting of a Faraday cage, an electron or a photo multiplier detector, and a charge-coupled device.

* * * * *